US00PP18364P2

(12) United States Plant Patent
Klemm

(10) Patent No.: US PP18,364 P2
(45) Date of Patent: Dec. 25, 2007

(54) ***PETUNIA* PLANT NAMED 'KLEC04065'**

(50) Latin Name: *Petunia×hybrida*
Varietal Denomination: KLEC04065

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/343,866

(22) Filed: Jan. 31, 2006

(51) Int. Cl.
*A01H 5/00* (2006.01)

(52) U.S. Cl. ..... Plt./356
(58) Field of Classification Search ..... Plt./356
See application file for complete search history.

(56) References Cited

PUBLICATIONS

UPOV–ROM GTITM, Plant Variety Database, 2006/04, GTI Jouve Retrieval Software, Citation for *Petunia* 'Klec04065', one page.*

* cited by examiner

*Primary Examiner*—Kent Bell
*Assistant Examiner*—June Hwu
(74) *Attorney, Agent, or Firm*—C. A. Whealy

(57) ABSTRACT

A new and distinct cultivar of *Petunia* plant named 'KLEC04065', characterized by its semi-trailing to cascading plant habit; freely branching growth habit; numerous double flowers that are yellow green in color; and good garden performance.

1 Drawing Sheet

Botanical designation: *Petunia×hybrida.*
Cultivar denomination: 'KLEC04065'.

BACKGROUND OF THE INVENTION

The present Invention relates to a new and distinct cultivar of *Petunia* plant, botanically known as *Petunia×hybrida,* and hereinafter referred to by the cultivar name KLEC04065.

The new *Petunia* is a product of a planned breeding program conducted by the Inventor in Stuttgart, Germany. The objective of the breeding program is to create new compact and freely branching *Petunias* with trailing plant habit and double flowers with attractive flower coloration.

The new *Petunia* originated from a cross-pollination made by the Inventor in 2002 of a proprietary selection of *Petunia×hybrida* identified as code number V 184, not patented, as the female, or seed, parent with a proprietary selection of *Petunia×hybrida* identified as code number V 185, not patented, as the male, or pollen, parent. The new *Petunia* was selected as a single plant from the resulting progeny of the stated cross-pollination in May, 2003 in a controlled environment in Stuttgart, Germany.

Asexual reproduction of the new cultivar by terminal vegetative cuttings since June, 2003, in Stuttgart, Germany has shown that the unique features of this new *Petunia* are stable and reproduced true to type in successive generations.

SUMMARY OF THE INVENTION

Plants of the cultivar KLEC04065 have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'KLEC04065'. These characteristics in combination distinguish 'KLEC04065' as a new and distinct cultivar:

1. Semi-trailing to cascading plant habit.
2. Freely branching growth habit.
3. Numerous double flowers that are yellow green in color.
4. Good garden performance.

In side-by-side comparisons conducted in Stuttgart, Germany, plants of the new *Petunia* differed from plants of the female parent primarily in flower color as plants of the female parent selection had light yellow-colored flowers.

In side-by-side comparisons conducted in Stuttgart, Germany, plants of the new *Petunia* differed from plants of the male parent selection in the following characteristics:

1. Plants of the new *Petunia* were more upright than plants of the male parent selection.
2. Plants of the new *Petunia* had double flowers whereas plants of the male parent selection had single flowers.
3. Plants of the new *Petunia* and the male parent selection differed in flower color.

Plants of the new *Petunia* can be compared to plants of the cultivar Kirimaji Double White, disclosed in U.S. Plant Pat. No. 14,281. In side-by-side comparisons plants of the new *Petunia* differed from plants of the cultivar Kirimaji Double White in the following characteristics:

1. Plants of the new *Petunia* were more upright and not as trailing as plants of the cultivar Kirimaji Double White.
2. Plants of the new *Petunia* and the cultivar Kirimaji Double White differed in flower color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Petunia*. The photograph comprises a side perspective view of a typical plant of 'KLEC04065' grown in a container.

DETAILED BOTANICAL DESCRIPTION

In the following description, color references are made to The Royal Horticultural Society Colour Chart, 1995 Edition, except where general terms of ordinary dictionary significance are used. Plants used the aforementioned photographs and following description were grown in a glass-covered greenhouse. Plants were about five months old when the photographs and description were taken. During the production of the plants, day and night temperatures ranged from 16° C. to 18° C. and light levels were about 20,000 lux.

Botanical classification: *Petunia×hybrida* cultivar KLEC04065.

Parentage:

*Female parent.*—Proprietary selection of *Petunia×hybrida* identified as code number V 184, not patented.

*Male parent.*—Proprietary selection of *Petunia×hybrida* identified as code number V 185, not patented.

Propagation:

*Type cutting.*—Terminal vegetative cuttings.

*Time to initiate roots, summer.*—About 18 days at 20° C. to 26° C.

*Time to initiate roots, winter.*—About 21 days at 20° C.

*Time to develop roots, summer.*—About 21 days at 20° C. to 26° C.

*Time to develop roots, winter.*—About 25 days at 20° C.

*Root description.*—Fine, fibrous; white in color.

*Rooting habit.*—Freely branching; moderately dense.

Plant description:

*Form/habit.*—Annual flowering plant; indeterminate; initially upright, then semi-trailing to cascading; uniformly mounded plant form. Freely branching habit with about six lateral branches and numerous secondary and tertiary lateral branches per plant. Pinching enhances development of lateral branches. Moderately vigorous growth habit.

*Plant height.*—About 16 cm.

*Plant diameter (area of spread).*—About 30 cm.

*Lateral branches.*—Length: About 16 cm. Diameter: About 4 mm. Internode length: About 3 cm. Texture: Pubescent. Color: 137C.

*Foliage description.*—Arrangement: Alternate; simple. Length: About 3 cm. Width: About 2 cm. Shape: Broadly elliptic. Apex: Acute. Base: Obtuse. Margin: Entire. Texture, upper surface: Sparsely pubescent. Texture, lower surface: Smooth, glabrous. Venation pattern: Pinnate. Color: Developing leaves, upper surface: 137A. Developing leaves, lower surface: 137C. Fully expanded leaves, upper surface: 147A. Fully expanded leaves, lower surface: 147B. Venation, upper surface: 146D. Venation, lower surface: 145A. Petiole length: About 2 mm to 8 mm. Petiole diameter: About 3 mm. Petiole texture, upper surface: Sparsely pubescent. Petiole texture, lower surface: Smooth. Petiole color, upper and lower surfaces: 145A.

Flower description:

*Flower type and habit.*—Double flowers; flowers face mostly outwardly; axillary. Freely flowering habit, about 13 flower buds and open flowers per lateral branch.

*Natural flowering season.*—Long day responsive; long flowering period, spring until frost in the autumn; flowering continuous during this period. Flowers persistent.

*Flower longevity on the plant.*—About one week.

*Fragrance.*—None detected.

*Flower size.*—Diameter: About 5.5 cm. Tube length: About 2.5 cm. Throat diameter, distal end: About 2 cm. Tube diameter, proximal end: About 4 mm.

*Flower buds.*—Length: About 3.5 cm. Diameter: About 2 cm. Shape: Oblong. Color: 150A.

*Petals.*—Quantity/arrangement: About 12 to 15 petals arranged in a rosette. Length from throat: About 2 cm. Width: About 3.5 cm. Shape: Roughly fan-shaped to obovate. Apex: Broadly acute with central points. Margin: Slightly crenate; undulate. Texture, upper and lower surfaces: Smooth, glabrous; satiny. Color: When opening, upper surface: 150A and 150D. When opening, lower surface: 150A and 150B. Fully opened, upper surface: 150B and 150D; venation, 150A; color becoming closer to 150D with development. Fully opened, lower surface: 150A and 150C; venation, 150A. Flower throat (inside): 151B; venation, 151B. Flower tube (outside): 151C; venation, 151C.

*Sepals.*—Arrangement/appearance: Single whorl of five sepals fused at base, star-shaped. Length: About 1.8 cm. Width: About 3 mm. Shape: Lanceolate to elliptic. Apex: Obtuse. Margin: Entire. Texture, upper and lower surfaces: Pubescent. Color, upper surface: 138A. Color, lower surface: 138B.

*Peduncles.*—Length: About 4 cm. Width: About 4 mm. Angle: Erect to about 75° from the stem. Strength: Moderately strong. Texture: Pubescent. Color: 137C.

*Reproductive organs.*—Stamens: Quantity per flower: About four. Anther shape: Roughly elliptic. Anther length: About 3 mm. Anther color: 1B. Filament: Less than 1 mm in length; white in color. Pollen amount: Moderate. Pollen color: 1A. Pistils: Quantity per flower: One. Pistil length: About 7 mm. Style length: About 5 mm. Style color: 2D. Stigma shape: Oval. Stigma color: 2B. Ovary color: 2D.

*Seed/fruit.*—Seed and/or fruit production has not been observed.

Disease/pest resistance: Plants of the new *Petunia* have not been noted to be resistant to pathogens or pests common to *Petunia*.

Garden performance: Plants of the new *Petunia* have been observed to have good garden performance. Plants of the new *Petunia* have been noted to tolerate temperatures from 8° C. to 45° C. and have excellent tolerance to rain and wind.

It is claimed:

1. A new and distinct cultivar of *Petunia* plant named 'KLEC04065', as illustrated and described.

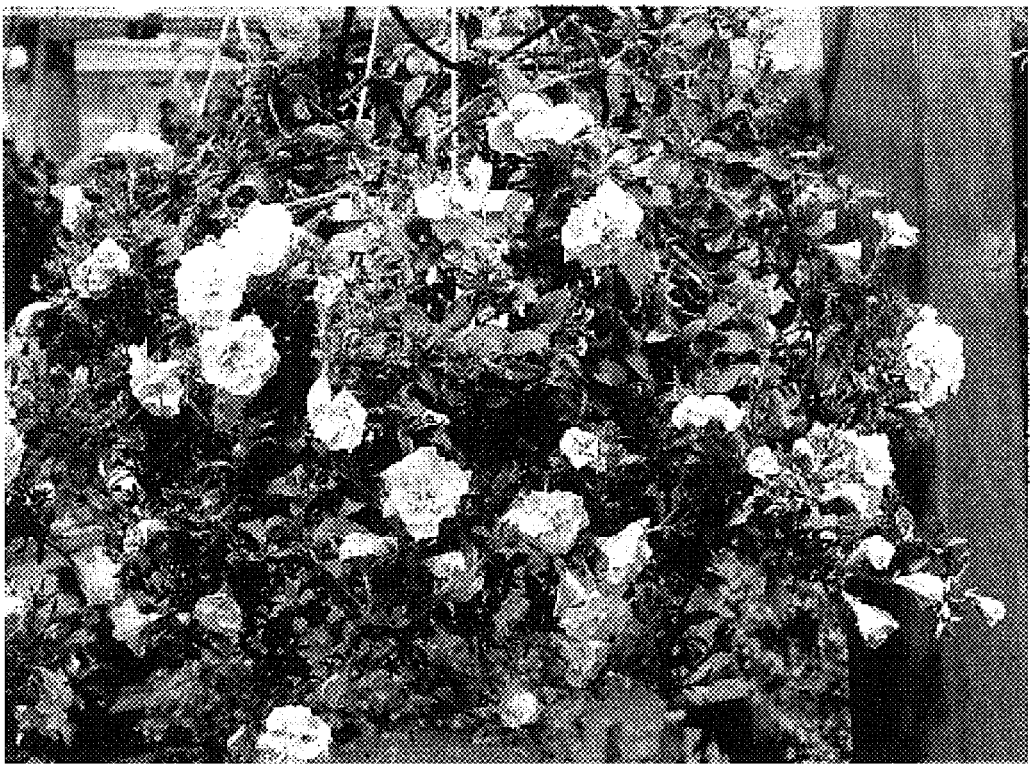

* * * * *